United States Patent [19]

Bernius et al.

[11] Patent Number: 4,933,551
[45] Date of Patent: Jun. 12, 1990

[54] REVERSAL ELECTRON ATTACHMENT IONIZER FOR DETECTION OF TRACE SPECIES

[75] Inventors: Mark T. Bernius, Pasadena; Ara Chutjian, La Crescenta, both of Calif.

[73] Assignee: The United State of America as represented by the Administrator of the National Aeronautics and Space Administration, Washington, D.C.

[21] Appl. No.: 361,531

[22] Filed: Jun. 5, 1989

[51] Int. Cl.[5] .................. H01J 46/26; H01J 37/12
[52] U.S. Cl. ........................... 250/288; 250/423 R; 250/427; 315/111.81
[58] Field of Search ............... 250/281, 288, 423 R, 250/424, 427; 315/111.81; 313/359.1

[56] References Cited

U.S. PATENT DOCUMENTS

| | | | |
|---|---|---|---|
| 2,978,580 | 4/1961 | Von Ardenne | 250/41.9 |
| 3,423,584 | 1/1969 | Erickson | 250/41.9 |
| 3,920,987 | 11/1975 | Anbar et al. | 250/282 |
| 4,468,564 | 8/1984 | Boyer | 250/427 |
| 4,649,278 | 3/1987 | Chutjian et al. | 250/423 |
| 4,689,574 | 8/1987 | Lim et al. | 250/427 |
| 4,742,232 | 5/1988 | Biddle et al. | 250/427 |
| 4,749,910 | 6/1988 | Hara et al. | 250/423 R |
| 4,749,912 | 6/1988 | Hara et al. | 315/111.81 |
| 4,782,235 | 11/1988 | Lejeune et al. | 250/423 |

Primary Examiner—Bruce C. Anderson
Attorney, Agent, or Firm—Thomas H. Jones; John R. Manning; Charles E. B. Glenn

[57] ABSTRACT

An in-line reversal electron, high-current ionizer capable of focusing a beam of electrons to a reversal region and executing a reversal of said electrons, such that the electrons possess zero kinetic energy at the point of reversal, may be used to produce both negative and positive ions. A sample gas is introduced at the point of electron reversal for low energy electron-(sample gas) molecule attachment with high efficiency. The attachment process produces negative ions from the sample gas, which includes species present in trace (minute) amounts. These ions are extracted efficiently and directed to a mass analyzer where they may be detected and identified. The generation and detection of positive ions is accomplished in a similar fashion with minimal adjustment to potentials applied to the apparatus.

5 Claims, 11 Drawing Sheets

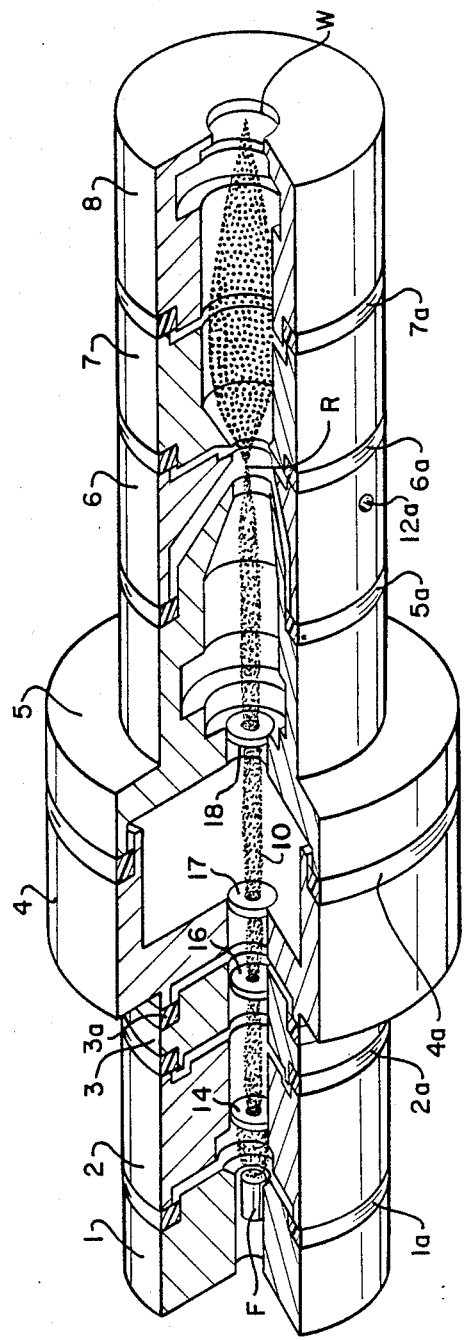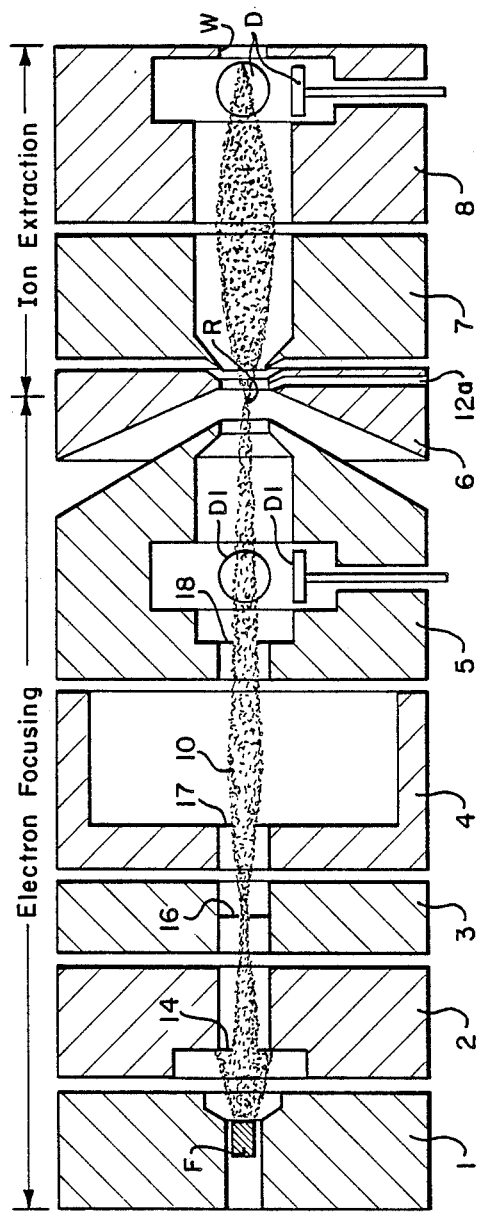
FIG.1(a)
FIG.1(b)

… …

REVERSAL ELECTRON ATTACHMENT IONIZER FOR DETECTION OF TRACE SPECIES

ORIGIN OF THE INVENTION

The invention described herein was made in the performance of work under a NASA contract, and is subject to the provisions of Public Law 96-517 (35 USC 202) in which the Contractor has elected not to retain title.

TECHNICAL FIELD

The invention relates to a high-sensitivity ion producing apparatus for trace species detection and more particularly to a combined in-line electron beam generator, trace species ionizer, and an ion extractor utilizing an electrostatic mirror field to form a planar wall of electrons having as low as zero kinetic energy for electron attachment to molecules of an analytic gas.

BACKGROUND ART

There exists a large number of molecules capable of attaching a zero or near-zero energy electron to form a negative ion. This ion may be the parent negative ion, or a fragment atomic or molecular ion formed via dissociative attachment. Energetically, the curve-crossing between the lowest neutral and negative ion states is made possible by the fact that the electron affinity of some atomic (e.g., F, Cl, Br, I) or molecular (e.g., CN) component is comparable to the dissociation energy of the neutral target. From symmetry considerations, the neutral-ion transition at zero electron energy often involves a transition between states of the symmetric irreducible representation, except possibly the halogen molecules. As such, the energy and symmetry requirement fulfill the s-wave threshold law in which the attachment cross section is $\sigma_A(E) \approx E^{l-\frac{1}{2}}$, where $l$ is the angular momentum component of the captured electron, and E the electron energy. For $l=0$(s-wave) attachment, A. Chutjian and S. H. Alajajian, Phys. Rev. A 31, 2885 (1985), were the first to demonstrate for the molecular case that the attachment process diverges as $\sigma_A(E) \approx E^{-\frac{1}{2}}$. This s-wave attachment divergence had been studied earlier in nuclear physics by others in thermal neutron capture by light nuclei. See E. P. Wigner, Phys. Rev. 73, 1002 (1948); H. A. Bethe, Rev. Mod. Phys. 9 69 (1937).

In an effort to utilize the divergent, zero-energy cross sections in $SF_6$ and the chlorohalocarbon compounds, a technique was disclosed by A. Chutjian, et al., U.S. Pat. No. 4,649,278, to focus an electron beam into an electrostatic mirror, where at the point of "reversal" the longitudinal electron energy was theoretically reduced to zero. In practice, only a fraction of electrons actually reach absolute zero energy at the point of reversal because of the lateral (transverse) velocity acquired in the electron gun. The beam of reversed electrons resembles a water fountain having a spray of finite vertical velocity and limited diameter up to the reversal region and a return spray of greater and spreading diameter. This spreading of the return flow of electrons results from a lack of shaped electrodes for electrostatic confinement in the reversal region where the electron beam achieves near-zero energies. Thus, after introduction of a beam of thermal-attaching molecules, negative ions were extracted from the collision center via the s-wave, dissociative attachment state, but no efforts were made in this earlier development to optimize electron current, reversal geometry, and extraction efficiency; nor were provisions made to minimize the transverse energy spread of the electrons at the reversal point.

In order to use this reversal electron attachment technique for ionization and ion-extraction of trace species at very low electron energies, the problem is to generate a large density of thermal electrons in the reversal region where attachment to molecules of extremely low concentration is to take place.

STATEMENT OF THE INVENTION

An in-line reversal electron, high-current ionizer-detector capable of focusing a beam of electrons to a reversal region of zero kinetic energy to produce negative ions through single collision electron attachment. By suitable adjustment of polarities, it can also produce positive ions through collisional ionization of the trace species by electrons of higher energy. Electron attachment to a molecular target in the reversal region produces parent or fragment negative ions through a zero-energy (s-wave) virtual state. The ions are pulsed out of the collision region to a quadrupole mass analyzer in line with the electron beam generator.

A planar wall of zero-energy electrons is created by focusing the electrons into parallel paths through shaped electrostatic fields to a plane where the electrostatic field effects a reversal of the electron trajectories while continuing to confine the electrons to the same parallel paths in the region of reversal. This provides a high density of thermal electrons of energies that approach and reach zero energy in the reversal region, with no transverse energy. The analytic gas is continuously introduced at the reversal region for ionization. Extracted ions are focused into a window of an in-line mass spectrometer operated in the negative-ion mode.

BRIEF DESCRIPTION OF THE DRAWINGS

FIG. 1(i a) is an isometric view of the electron gun, electron reversal, and ion extraction lens systems of the present invention partially sectioned, and FIG. 1(b) is a schematic cross section diagram of the structure in FIG. 1(a).

THEORY OF RESONANCES

Figure 2:
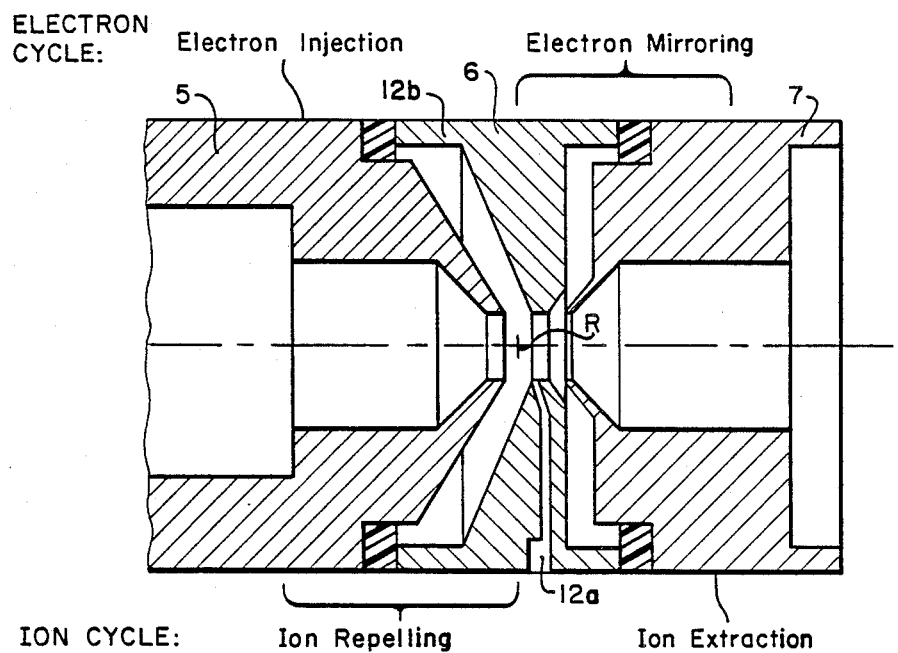
FIG. 2 illustrates details of the shaped electrodes shared for electron reversal and ion extraction.

The formal theory of resonances, virtual states, bound states, and their behavior at threshold has been given within several frameworks and applied in specific instances to diatomic and polyatomic scattering. In the following paragraphs, a heuristic picture of the attachment process is presented, concentrating somewhat more on a physical picture rather than on the theoretical formalism.

For electrons e(E) of energy E and a target molecule AB in vibrational state v, the process of electron attachment

$$e(E) + AB(v=0) \rightarrow AB^-(v>0) \tag{1a}$$

and dissociative attachment (DA)

$$e(E) + AB(v=0) \rightarrow A + B^- \tag{1b}$$

constitute major reaction channels that influence the behavior of the upper atmosphere, lasers, electrical discharges, lamps, gaseous insulators, circuit breakers and high-power diffuse-discharge switches. They are also the principal reaction channels upon which the electron-capture detector (ECD), used in chromotographic studies, is based: namely, that one influences the current in a detection circuit by converting a mobile electron into a sluggish negative ion via Equations (1a) and (1b).

The model considered here is one in which a new bound, virtual negative-ion state is born at threshold, i.e., with a large s-wave component. See J. P. Gauyacq and A. Herzenberg, J. Phys. B 17, 1155 (1984). The mechanism of electron capture is a nonadiabatic coupling of the neutral target and a negative-ion state formed by the "loosely bound" electron. The virtual state is associated with a pole on the negative k-axis in the complex k plane. The effect of this pole, lying slightly below the origin, is to cause at low electron energies enhancement of the amplitude of the electron wavefunction at the target relative to the incident wave. No angularmomentum trapping and time-delay is involved, such as in a shape or Feshbach resonance at higher electron energies. See, for example, A. Herzenberg and B. C. Saha, J. Phys. B 16, 591 (1983). The enhancement of the electron's wavefunction at the molecular boundary is brought about by constructive interference between the incoming s-wave of the form (sin kr)/kr, and the outgoing wave of the form (cos kr)/kr.

In the limit of small energy kr<<1, the ratio of amplitudes becomes $$\left(\frac{\cos kr}{kr}\right) / \left(\frac{\sin kr}{kr}\right) = \approx (kr)^{-1} \approx << \frac{\lambda}{r} \tag{2}$$

where $\lambda$ is the reduced deBroglie wavelength, and r is the electron-molecular center distance. For $r \approx 4a_0$ and $k=0.027$ au (0.01 eV), this enhancement is a factor of 9.2 in amplitude, or 85 in intensity.

Following the treatment of Guayacq and Herzenberg cited above, one may express the attachment of DA cross section $\sigma_a(E)$ as $$\sigma_A(E) = \frac{4\pi^2}{\sqrt{2}} |A_{v0}|^2 E^{-1/2} \tag{3}$$

where E is the electron energy in au, and $A_{v0}$ is the amplitude of the wavefunction $\Psi(r,R)$ in the time-reversed calculation for an ion-atom collision.

$$\Psi(r,R) = \sum_v A_v \chi_v(R) \frac{\exp(ik_v r)}{r} \tag{4}$$

Here, r is the electron'distance from the $AB^-$ center of mass, R the $A^-$—B nuclear distance, $k_v$ the electron momentum as it collides with the vibrational level v in $AB^-$, and $X_v(R)$ is the vibrational wavefunction of level v as a function of internuclear distance. Equation (4) describes a spherical outgoing electron wave which was detached in the $A^-$—B collision, leaving AB(v) in the $v^{the\ vibrational\ level}$. The collision corresponds to the time-reversed process $AB(v) + e \rightarrow AB^-(v')$ so that the scattering cross sections are related by detailed balance. The important feature of Equation (3) is that, in the limit of E→0, the outgoing amplitudes $A_v$ become slowly varying with respect to $E^{-\frac{1}{2}}$ so that the attachment cross section exhibits the $E^{-\frac{1}{2}}$ divergence.

The negative ion thus formed can have several fates. If a dissociative channel is energetically open, the ion will fragment in the course of a single vibration. An example of this dissociative attachment [Equation (1b)] is the breakup $e + CCl_4 \rightarrow CCl_3 + Cl^-$. If the negative ion is stable with respect to dissociation, then the total electron vibrational energy will be distributed throughout the molecular ion normal modes: its vibrational phase space is dramatically increased to the point where one has a quasicontinuum of translation-like energy levels. Such a state can exist for times on the order of tens of microseconds, after which it may (a) autoionize to the neutral target state, (b) be stabilized by collision with another molecule, or (c) become detected in an experiment prior to autoionization.

The present invention efficiently generates molecular ions via negative or positive-ion formation at electron energies from zero electron volts to high energies (50 eV or greater). By optimizing instrumental factors, these molecules can be detected at the parts-per-billion level and better.

DETAILED DESCRIPTION OF THE INVENTION

(a) Overview

Referring to a schematic diagram of the apparatus shown in FIGS. 1(a) and 1(b) for effecting electron capture (negative-ion formation) to molecules at low electron energies, a high current-density electron beam 10 is brought to a well-controlled reversal region R such that at the reversal point, the lateral and longitudinal components of the electron's kinetic energy are zero. A sample gas of interest is introduced into the reversal region R through a port 12a, and owing to the extremely large attachment cross section of this interaction energy, an extremely efficient means for production of negative parent molecular ions is provided.

High-speed pulsed electronics switch the apparatus of FIG. 1 from molecular negative-ion generation (employing electron optics described below) to the collection and focusing of these ions (employing in-line ion extraction optics described below) to a suitable means of performing mass analysis and detection, such as a quadrupole analyzer shown in FIG. 3(c). The shaped electrodes (electron optical components) 1–8 are individually controlled, with the electrode 6 shared for electron injection and ion repulsion, as shown in FIG. 2, during both the electron injection-reversal cycle, and the ion extraction cycle, providing an efficient instrument for analysis of trace species. In actual practice, the electron beam is pulsed on for about 50 μs and then off. After about 2 μs, in-line ion extraction electrodes are pulsed on. Ion collection efficiency is on the order of 100%, and estimated detection limits can be on the order of 100 ions per cubic centimeter of sample gas.

In accordance with a further feature of the invention, it is possible to not only bring the electrons to a zero-energy (reversal) focus in the interaction region R but to a higher energy focus as well in order to either (a) generate negative ions through attachment processes occurring at near zero electron energies, or (b) effect positive ionization of the trace species at higher electron energies. The ion extraction in both cases is carried out with the same apparatus, except that extraction potentials in the case of positive ion extraction are reversed.

Referring to FIG. 1(a) and 1(b) in more detail, electrons are generated at an indirectly heated cathode F having a planar face, and focused by shaped annular electrodes (lens elements) 1–6 to the reversal region R. Insulating spacers 1a through 5a shown in FIG. 1(a) isolate the electrodes 1–6 so that they may be operated at independent potentials in providing an electrode beam with reversal at the region R. The gas sample of target trace species is continuously introduced at this point through the port 12a and vented through a larger port 12b, and either negative ions are formed by attachment of electrons in the energy range 0–20 eV, or positive ions are formed by bombardment with electrons having energy of about 40 eV.

Figure 6A:
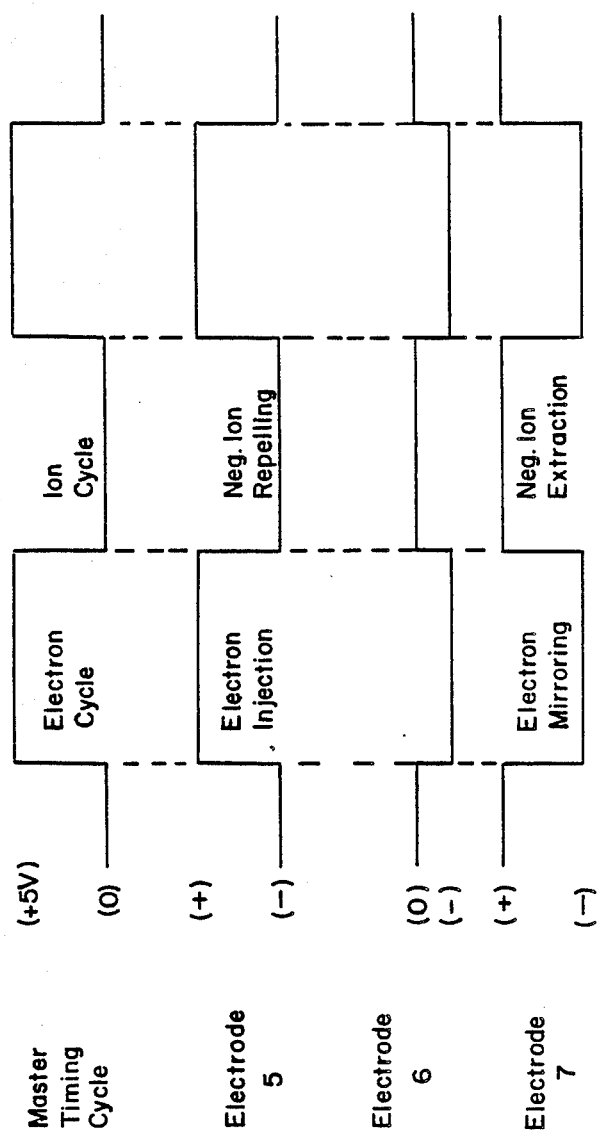
FIGS. 6(a) and (b) illustrate the electrode pulsing sequence for extraction of negative and positive ions, respectively.

The electrons are injected by impressing suitable negative and positive voltages on respective annular electrodes 5, 6 and 7, as shown in FIGS. 6(a) and (b) for negative and positive ions, respectively. The voltages are then switched for ion extraction and within 2 μsec the negative ions are extracted through a window W. Insulating spacers 6a and 7a (optional) shown in FIG. 1(b) isolate the electrodes 6, 7 and 8 so that they may be operated at independent potentials while producing the electrons beam and then while extracting ions from the region R. This sharing of electrodes for electron injection and reversal and for ion extraction is illustrated in FIG. 2. The duty cycle of the voltage switching can be 50%, with 100% extraction efficiency of the ions during each ion cycle. Orthogonal deflectors $D_1$ shown in FIG. 1(b) may be used to provide small electrostatic deflection forces on the electron beam for fine tuning of the beam position at the center (axis) of the region R.

The negative ions are focused at the plane of the exit window W by electrode 8 biased at a potential, negative for negative ions and positive for positive ions, to confine the ions within a spot size, and with a divergence angle and final energy appropriate to either a quadrupole mass analyzer or time-of-flight analyzer. Orthogonal deflectors $D_2$ shown in FIG. 1(b) may be used to provide small electrostatic deflection forces on the ion beam for fine tuning of the beam position at the center (axis) of the exit window W. It should be noted that a range of final electron energies can be provided at region R by establishing the reversal point between electrodes 5 and 6 relative to the electrode 7.

Figure 3B:
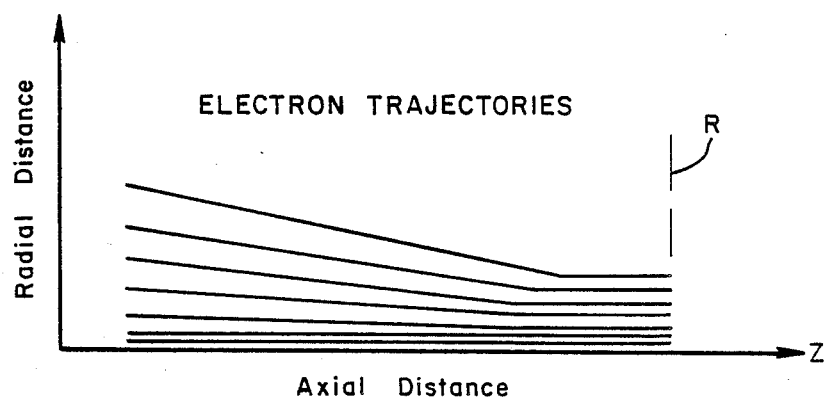
FIG. 3(b) is a graph of the reversal region showing the time-reversed Pierce-element behavior, resulting in a vertical "wall" of electrons at R with zero transverse and longitudinal energy.
Figure 3A:
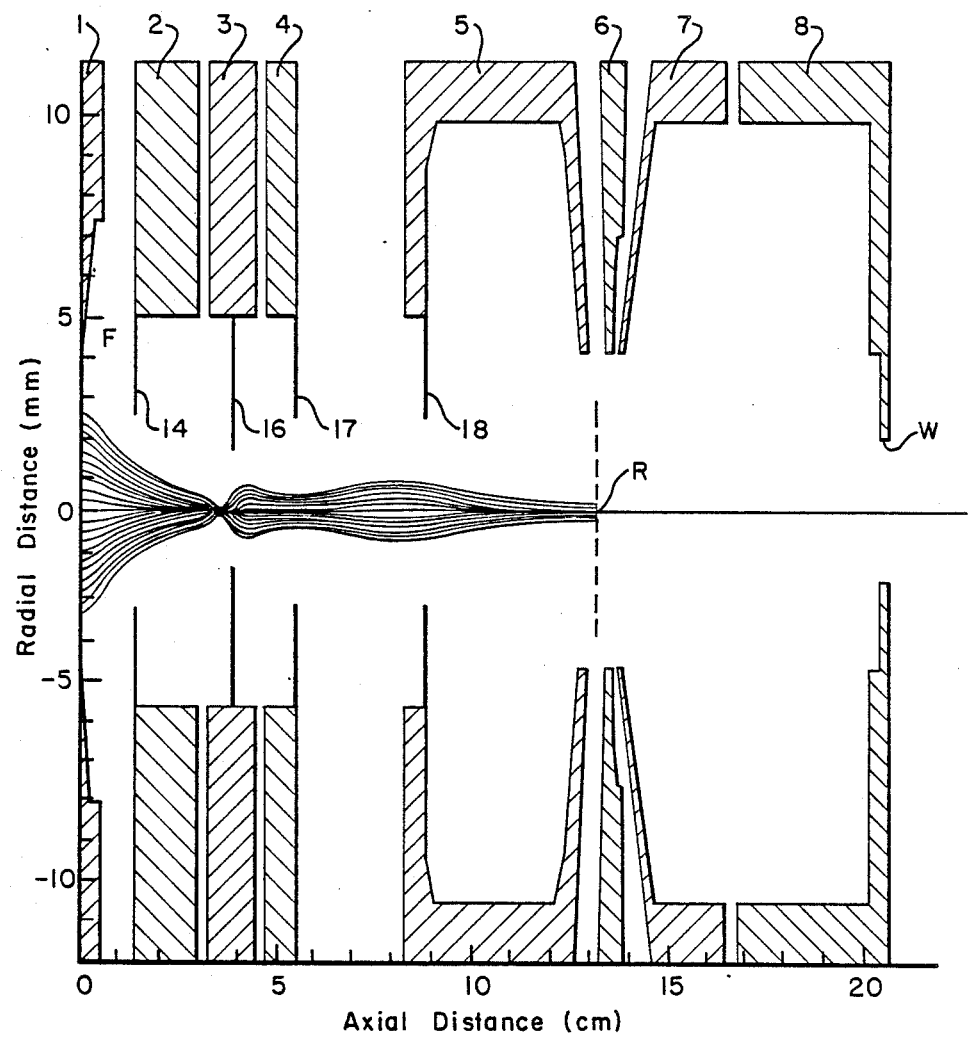
FIG. 3(a) is a graph of electron trajectories calculated up to a reversal region R during the "electron on" half cycle.

Trajectories of electrons and ions were calculated using a full space-charge formulation, in which computerassisted design techniques are used to solve for the electrode geometry and potentials necessary to achieve the final trajectories plotted in FIGS. 3(a), (b) and (c). The trajectories achieved are such that the reversed electron path exactly retraces itself as it returns toward the heated cathode F, thus providing absolute zero-energy electrons in the reversal region R. This is accomplished by carefully choosing the shape of the electrodes 5–7. If desired, an electron beam for nonzero bombardment may be provided to cross the sample gas target inlet positioned twice, once while proceeding left to right and once while returning right to left. This nonzero energy electron beam affords a factor-of-two increase in effective electron beam density at the region R, and hence of ultimate ion detection sensitivity.

(b) Electron Cycle and Ion Cycle

Electrostatic field penetration or overlap, discussed by M. T. Bernius, K. F. Man and A. Chutjian, Rev. Sci. Instrum. 59, 2418 (1988), has been incorporated in the present invention. The primary electron source is the heated cathode F which is planar and whose optical properties have been presented by Bernius, et al., in the paper just cited. The electrons can be accelerated up to 600 volts and then extracted through an aperture 14 in electrode 2. Electrode 3, in which there would be significant field penetration except for an aperture 16 placed therein, decelerates the beam and forces a crossover in the neighborhood of its aperture. This crossover is imaged at the reversal region R by the shaped electrodes (projector lens elements) 4–5 immediately following. The final electrode 5 of the electron gun has the deflection capability to center the beam on axis with fine tuning by electrodes $D_1$. A computed trajectory is shown in FIG. 3(a). Note that in the graphs of a computer model shown in FIGS. 3(a), (b) and (c) the scale of radial distance has been magnified by a factor of ten for clarity relative to the axial distances.

The beam is finally focused at a plane near the axial midpoint of the shaped electrodes (electrostatic mirror elements) 5–6 which define the reversal region R. These mirror electrodes 5–6 are so shaped (designed) as to facilitate formation of a collimated beam coming to zero longitudinal and radial velocity at the reversal plane, as shown in FIG. 3(b). Therefore optical conditions to assure a proper match between electron trajectories exiting the projector lens and those necessary to achieve zero kinetic energy at the reversal plane where the sample gas is injected are maintained by proper choice of voltages on the electrodes 5 and 6. The following trajectories are then observed: paraxial rays of small angular divergence coming to a focus are "straightened out" to parallel trajectories in the last few millimeters of beam path, as depicted in FIG. 3(b). The electrons, now parallel to the optical axis, come to a stop with zero velocity in both longitudinal and radial components of the particle's velocity at the focal plane R, and reverse direction. In this way, the optical principle of reciprocity is used to assure complete reduction of the beam's energy, as will be more fully discussed below.

The electron gun electrodes 1-5 and electron mirror electrodes 6-7 are designed to focus a 400 μA primary beam diameter to a 130 μm diameter in the reversal region. This are possible because the shaped electrodes compensate for space charge. Beams of less current (and lower voltage) are easily accommodated with proper retuning of the operating electrode voltages. In actuality, the electron beam is not entirely of uniform electron energy, even though the electrode shapes and apertures along the path of the beam are intended to favor electrons of uniform energy. An aperture placed at the major focal point of a chromatic lens will perform energy selection, favoring that energy band whose focal point corresponds to the aperture plane as a function of the aperture size. Likewise, an aperture stop placed at the Gaussian image plane will also improve chromatic filtration when dealing with small cylindrically-symmetric object sources undergoing demagnification. See G. F. Rempfer and M. S. Mauck, J. Appl. Phys. 63, 2187 (1988). Therefore, in practice, an ensemble of reversal conditions will exist in the neighborhood of the calculated reversal plane R.

The terms "reversal plane" and "reversal region" are used to refer to substantially the same area of the electron beam path but with the more precise term "reversal plane R" as indicated in FIG. 3(b) when referring to the place of reversal of the electrons, and the less precise term "reversal region R" when referring to the place of ionization of the sample gas. Note that the reversal plane R may be shifted to the right along the Z axis for nonzero energy ionization, i.e., for producing positive ions. For this reason, special provisions are incorporated in the design of the ion-focusing electrodes 6-8 to select the position of the reversal plane, and to focus ions found there into the acceptance window W of the quadrupole mass analyzer 20 shown in FIG. 3(c). The shaped electrodes 6 and 7, coupled with shaped electrodes 7 and 8, are quite selective. By matching operating voltages with aperture size on the exit window W of electrode 8, only those ions from a depth Δz of the reversal region R will be focused, mass analyzed and detected. For the present example of the invention, Δz=0.8 mm was used.

(c) Electron Focusing and Ion Extraction

Figure 3C:
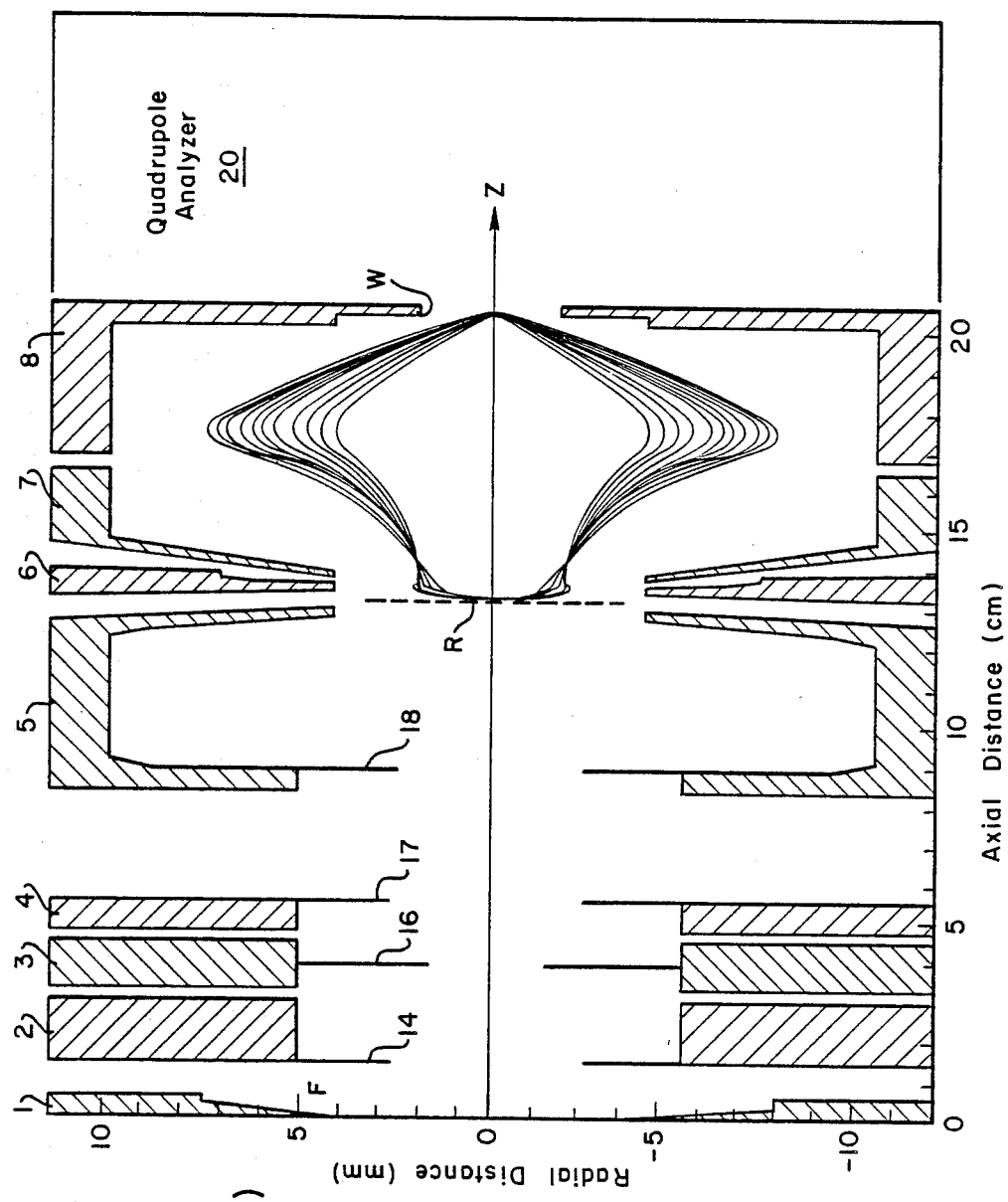
FIG. 3(c) is a graph of ion trajectories calculated up to an entrance window W of a quadrupole analyzer during the "ion on" half cycle.

The electron-focusing and ion-extraction operations shown in FIGS. 3(a) and 3(c) are alternately switched on, as will now be described with reference to FIG. 6(a). Electrons are focused and reversed at region R during one-half of a square-wave switching cycle timing signal, then shut off by applying a large negative voltage on annular shaped electrode 5. After a few microseconds into the second half of the cycle, the ions are extracted by a positive voltage on annular shaped electrodes while electrode 6 is held at zero volts. Ion trajectories are shown in the computed simulation of FIG. 3(c). Alternating between the electron cycle and the ion cycle is thus accomplished by switching voltages applied to shaped electrodes 5-7. Those voltages are applied sufficiently fast so that the generated negative ions cannot drift from their origin by more than about one-third the lens diameter during the time it takes to switch voltages.

During an electron cycle indicated in FIG. 2, the shaped electrode 5 is pulsed to a positive voltage (+40 V) for focusing the electron trajectories as shown in FIG. 3(b), while the electrodes 6 and 7 are both held at a potential sufficiently negative (−10 V) to produce electron reversal at the plane R. Electrodes 1, 2, 3 and 4 remain at their selected positive potentials with respect to the cathode voltage for shaping and focusing the electron beam 10. Following an electron cycle, an ion cycle indicated in FIG. 2 is initiated by pulsing the electrode 7 to a high positive voltage (+850 V) and the electrode 5 to a negative (−200 V) potential while the electrode 6 is switched to zero volts, as shown in FIG. 6(a). This repels negative ions away from the region R while the positive electrode 7 extracts the ions. The shaped electrode 8 remains at a positive potential for focusing the ion beam into the window W.

Figure 6B:
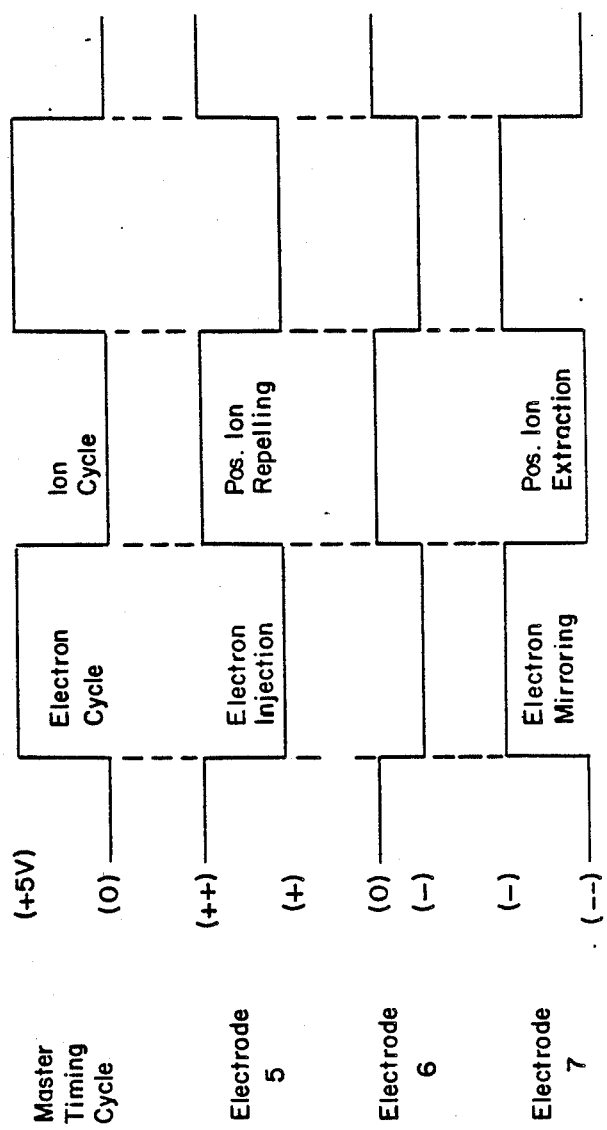
Figures 7A, 7B, 7C:
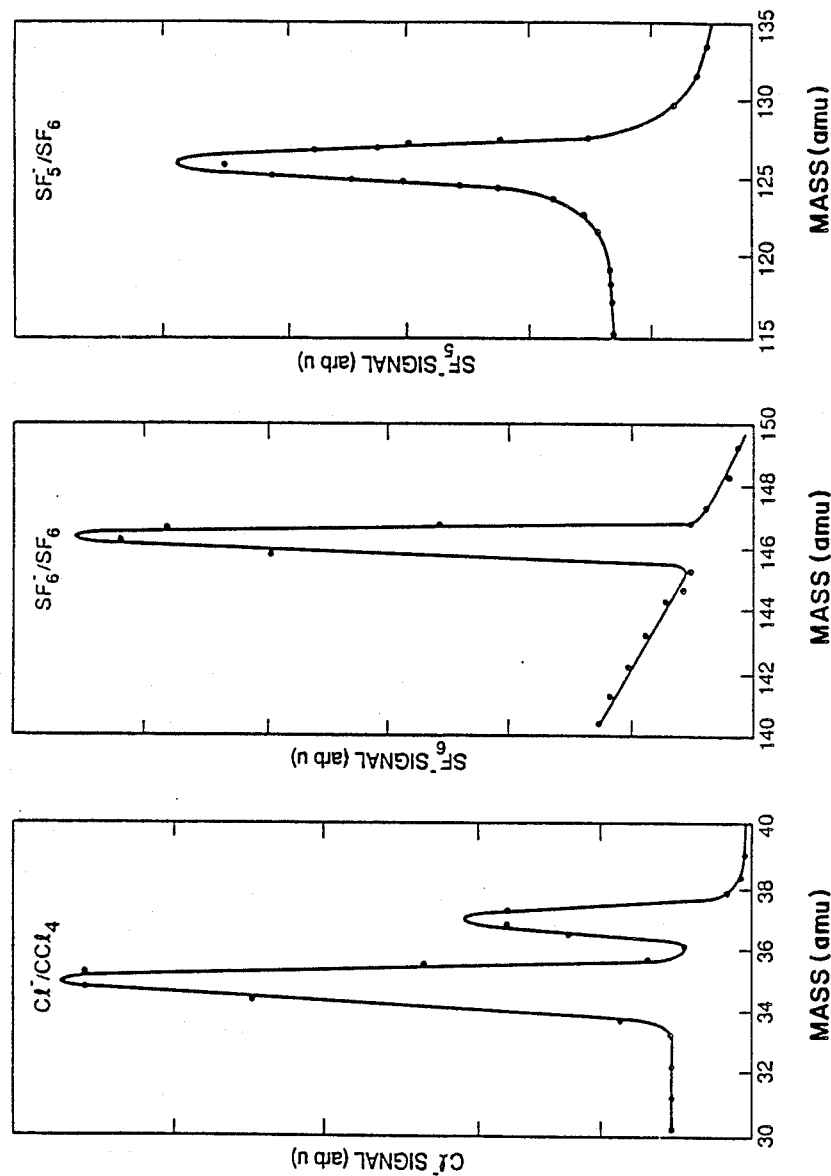
FIGS. 7(a) through (f) illustrate mass spectra of attachment and dissociative attachment in $CCl_4$, $SF_6$, $CHCl_3$, $1,1,2-C_2Cl_3F_3$ and $c-C_6F_{10}$ achieved with the present invention. The resonances in FIGS. (c) and (d) are at nonzero electron energy while those in FIGS. (a), (b), (e) and (f) correspond to virtual states at zero energy.
Figure 7F:
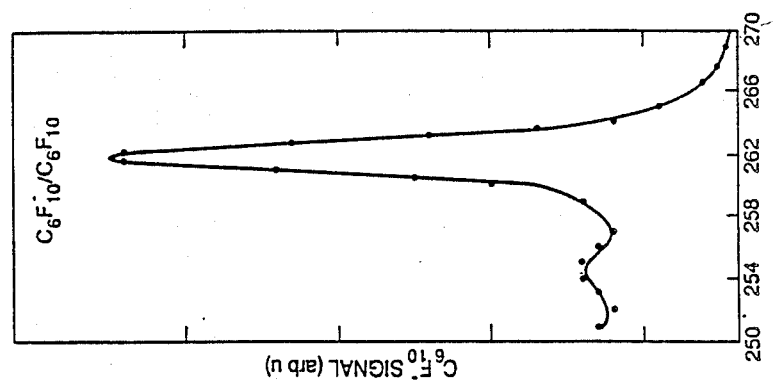
Figure 7E:
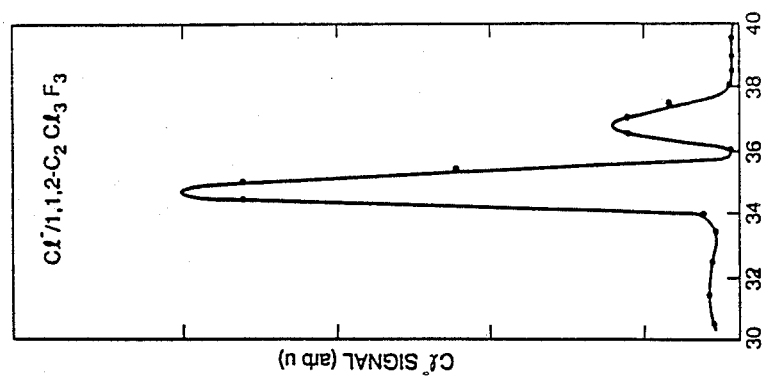
Figure 7D:
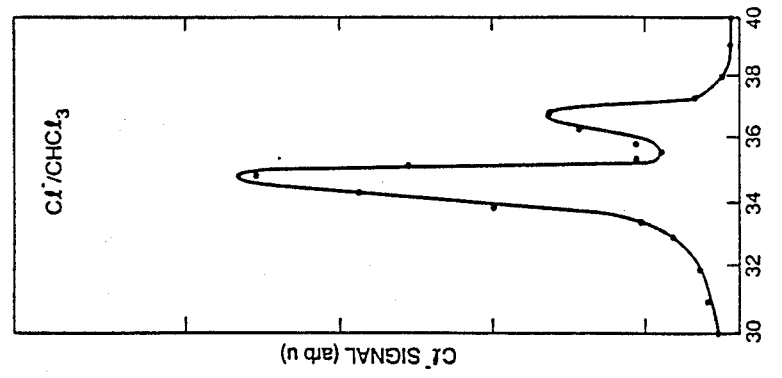

For producing positive ions by bombardment with electrons, the reversal plane is adjusted further toward the electrode 7 in order that the electrons crossing the path of the sample gas introduced through the port 12a will have a higher energy (about 40 eV). This is accomplished by changing the switching voltages, as shown in FIG. 6(b), to provide a positive voltage on electrode 5 in order to continue focusing electrons in parallel paths, as shown in FIG. 3(b), and to provide a more negative voltage on the electrode 7. For extraction of the positive ions, the voltages applied to the electrodes 5 and 7 are reversed in polarity during the ion cycle. By using high-voltage, full-floating switching electronics responsive to the signal for switching cycle timing, as described by the inventors in a paper titled "High-voltage, full-floating 10-MHz square-wave generator with phase control,"Rev. of Sci. Instr., 60, 779 (1989), and in a copending U.S. patent application filed Mar. 31, 1989, Ser. No. 07/331,160, fast switching of the lens potentials are achieved.

Figure 4A:
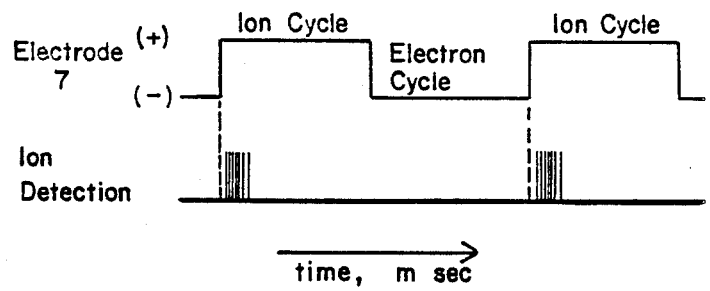
FIG. 4(a) illustrates typical ion arrival-detection characteristics as seen on an oscilloscope for $Cl^-$ production from $CCl_4$ during an ion cycle and an electron cycle (square wave train) with ions arriving for detection shortly after the ion cycle is turned on, and FIG. 4(b) shows in greater detail the ions arriving shortly after the ion cycle is turned on in the graph of FIG. 4(a) where the ion burst arrives at the detector approximately 15 μs after ion extraction voltage is applied, which corresponds to the chlorine ion's time-of-flight from the ion extractor through the quadrupole and to the detector.
Figure 4B:
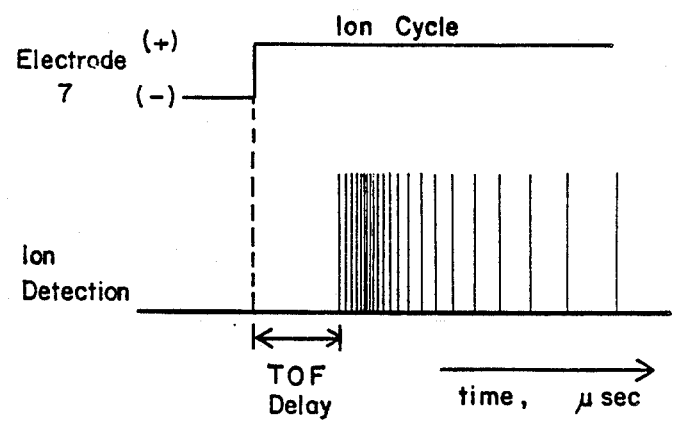

A fast (50 ns) rise-time high-frequency square-wave generator is disclosed in that paper and patent application that is capable of switching between arbitrary voltages of high potential difference using high-current drivers for power field-effect transistors. Switching signals are provided to the high-current drivers from a logic network through optoisolators. High-voltage square-wave pulse trains of controllable phase are produced in the logic network. Other phase-adjust logic networks may, of course, be employed as well as other drivers for high power field-effect transistors. Square-wave pulse trains of variable duty cycle are used, and they permit easy observation of the ion pulses as they arrive synchronously during the ion on cycle. Typical ion arrival-detection characteristics are shown in the timing diagram of FIG. 4(a) where the waveform A represents the timing of the high-voltage square wave applied for ion extraction, and the waveform B represents the time-of-flight (TOF) of the ions which is complete after 25 μs. FIG. 4(b) illustrates the TOF response for one ion extraction period shown in FIG. 4(a). Note that the ion intensity at the detector of the quadrupole analyzer 20 shown in FIG. 3(c) drops off quickly once the signal associated with the "ion on" cycle is initiated. The ion signal burst arrives at the detector approximately 15 μs after the ion extraction voltage is applied as shown in FIG. 4(b). That time delay corresponds to the TOF of the chlorine ions from the reversal region R after production from CCl₄.

Extracted ions are focused onto the exit window W with a final energy, angular divergence and diameter suitable for the quadrupole mass analyzer 20 shown as a functional block in FIG. 3(c). Detection is achieved in such a mass analyzer by means of a channel-type electron multiplier and pulse amplifiers.

DESIGN OF THE IONIZATION REGION

1. The Electrostatic Mirror

Typical electron filament sources employ a Pierce geometry [J. R. Pierce, J. Appl. Phys. 11, 548 (1940)] for the efficient electron extraction while maintaining a parallel axially-flowing beam. This is accomplished by the electrostatic potential that the electrode geometry sets up which counteracts space-charge repulsion of the electrons during initial acceleration from the filament. It therefore follows that a reverse-Pierce geometry would facilitate maintaining an axial beam during deceleration by the optical principle of reciprocity. In practice, slight modifications are necessary, which will now be explained.

In one dimension, the Child-Langmuir space-charge law can be rearranged to show that the potential varies as the 4/3 power of the distance x between the cathodic emitter and the accelerating anode (Wehnelt electrode), viz:

$$V(x) = \left( \frac{9}{4\epsilon_o \sqrt{2q/m}} \right)^{2/3} J^{2/3} x^{4/3} \tag{5}$$

where V represents the emitter-accelerator potential, J is the magnitude of the current density, $\epsilon_o$ is the permittivity of free space and $q/m = 1.759 \times 10^{11}$ C kg⁻¹ for electrons.

Figure 5B:
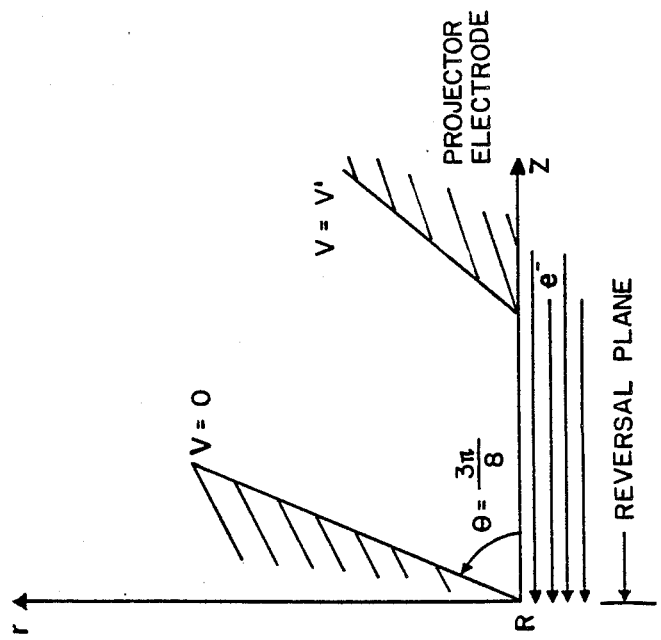
FIG. 5(b) illustrates time-reversed electron flow in an analogous Pierce geometry (in cylindrical-polar coordinates) to achieve electron reversal at a point R of an imaginary cathode.
Figure 5A:
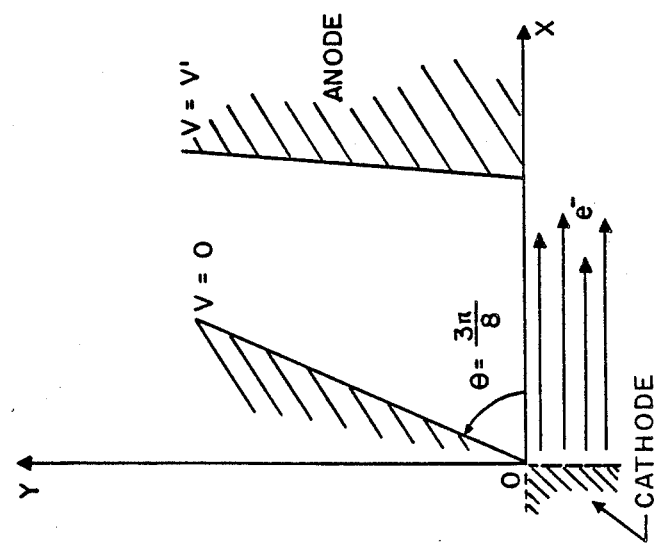
FIG. 5(a) illustrates Pierce extraction geometry showing the inclined V and V' surfaces used to extract a linear flow of electrons from the planar electron emitter in rectangular coordinates.

A two-dimensional description in rectangular coordinates if found by conformal transformation where now substitutions are made by orthogonal functions satisfying the Cauchy-Riemann relations. It will be found that the V=0 surface originates at the origin (x,y=0) and will be a straight line subtending an angle $\theta = 3\pi/8$ to the x-axis. This represents an electrode placed around the cathode F and typically held at the same potential. The anode surface is more difficult to evaluate analytically, but the numerical trend leads to a Wehnelt electrode shape that is less conical near the beam path. This is the well-known Pierce-electrode geometrical arrangement and is shown in FIG. 5(a). The operation described is independent of time, hence under time-reversal a beam parallel to the optical axis will remain paraxial as it is decelerated in the same electrostatic arrangement.

By numerical simulation a modified geometry was calculated for the cylindrically-symmetric case which would also serve as an electrostatic mirror, achieving paraxial flow during deceleration. In this case, the reverse-anode would be more conical than the reverse-Pierce element, as shown in FIG. 5(b). Then, at the reversal point (the position of the imaginary cathodic filament), the absolute velocity of the space-charge limited electron beam would be zero, with no tangential component.

2. Ion Extraction

Ions are formed by electron attachment or DA to the target gas in the electron-reversal region R. To prevent a large current of electrons from reaching the window W and the mass analyzer, it is desirable to switch off the electrons and wait for electrons to disperse under coulombic repulsion. This time interval should be chosen short enough so that the slower-moving ions migrate only slightly from their point of origin. In practice, the switching-off is accomplished in 50 ns, and the ion extraction voltage (50 ns risetime) is initiated 0.5–3 μs later.

In addition, the bulk of ions are inconveniently in the middle of the electron mirror, not in a position conducive to easy extraction. Therefore, an adequately shaped ion extractor electrode, acting under pulsed high potential out of phase by a half cycle to the electron focusing system is employed for efficient ion collection. All electrode shapes have been optimized by computer-assisted numerical simulation of the potential field and the equations of motion, taking into consideration the thermal drift of the ions due to their kinetic energy at onset.

3. The Combined System

Combining the electron reversal and ion extraction geometry is achieved by sharing the middle electrodes 6 as is shown in FIG. 2, and in FIGS. 6(a) and (b). The two electrodes 6 and 7 form the final mirror field. The electrode 5 forms the initial field of the electrostatic mirror. During the ion extraction cycle, electrode 5 is biased to repel the ions formed between electrodes 5 and 6 while electrode 7 is held at a high potential appropriate for ion extraction. The potential electrode 6 is chosen to provide suitable lens action at the interfaces of electrodes 5 and 6, and electrodes 6 and 7 improving the efficiency of ion extraction in this region to 100%.

Shown also in FIG. 2 is the gas inlet annular port 12a in electrode 6. Considering only molecular gas flow under an operating vacuum of 10⁻⁸ torr, the effluent gas forms a narrow "jet" distribution. Its greatest density is thus reasonably confined to the midpoint on the axis between electrodes 5 and 6, as shown in FIGS. 3(a) and 3(c).

By adjusting the voltages properly, the reversal point can be moved to the right of the molecular beam's greatest density so as to achieve nonzero electron energy interactions in the collision region. In practice, electron bombardment energies as high as 200 eV have been achieved. This tunable arrangement allows for the production of positive ions, typically achieved at bombarding energies of 50–80 eV. The system then behaves as a conventional residual gas analyzer.

TEST RESULTS

(a) Experimental Arrangement

The present system accomplished mass analysis using an Extrel quadrupole mass spectrometer which can provide unit mass resolution up to 500 amu. The arrangement of FIGS. 1a and 1b and the quadrupole mass filter were housed in a stainless steel UHV chamber, lined with 1.5 mm thick mu metal to shield external magnetic fields to less than 10 mG over the electrode region from electrodes 3 to 8, inclusive. The chamber was pumped by a 1500 l/s (air) Edwards oil-diffusion pump with a liquid nitrogen trap. Operating pressures with gas load were between $1.0 \times 10^{-8}$ and $5.0 \times 10^{-7}$ torr, with a base pressure of $5.0 \times 10^{-9}$ torr.

Samples of high purity gases and liquids were obtained from the Matheson Gas Co. and Aldrich Chemical Co. The liquids involved were housed in special pyrex ampules and were subjected to at least five freeze-thaw cycles to remove trapped air. Prior to entering the port 12a of the system, a precision leak valve was employed to deliver reproducible gas flows to the electron-reversal region. All lines and valves were wrapped in heating tape and warmed to 350K to prevent condensation and/or adsorption of the vapors in the apparatus.

The data handling system consisted of a preamplifier wired to the quadrupole's channeltron detector, which delivers signals to a TTL digital circuit producing 5-volt pulses corresponding to counts above a preset threshold. Signal intensity per mass is read on either an Ortec count-rate meter, or on a single-channel scaler. No provision was made for computer control or multichannel scaling analysis.

(b) Sample Runs

In order to demonstrate the operation of the system FIGS. 7(a-f) show electron attachment and DA results in $CCl_4$, $SF_6$, $CHCl_3$, $1,1,2-C_2Cl_3F_3$ and $c-C_6F_{10}$. These results demonstrate the formation of parent negative ions via virtual states at zero electron energy shown in FIG. 7(b,f); DA fragments via virtual states at zero energy shown in FIG. 7(a,e); DA fragments via real states at nonzero energy corresponding to a reversal point to the right of R shown in FIG. 7(d) (the $CHCl_3$ resonance lies at 0.37 eV); and parent negative ions via real states at nonzero energy shown in FIG. 7(c) (the $SF_5^-$ resonance lies at 0.39 eV). The experiments were also able to resolve clearly the $^{35,37}Cl^-$ isotopes in FIGS. 7(a,d,e). The ratio of peak heights varies with the quadrupole pole bias, and does not necessarily correspond to the natural isotope ratio.

The question naturally arises as to the sensitivity of the ionization system for detection of the molecular targets of FIG. 7(a-f). To determine the sensitivity, one of the targets, $CCl_4$, was chosen and the method of standard additions was used. A mixture of $CCl_4$ in nitrogen was prepared, and the $Cl^-$ count rate was measured as a function of the concentration C of the mixture.

Mixtures were prepared in an all stainless steel vacuum system capable of being heated to 350K. Reagent grade $CCl_4$, having undergone eight freeze-thaw cycles was mixed with $N_2$ (99.99% purity) in a concentration ratio C (particle density) =1 (pure $CCl_4$) to $5 \times 10^{-7}$. The quadrupole mass spectrometer was tuned on mass 35, and the $Cl^-$ signal measured at each C to a statistical accuracy of 3%. Care was taken in the concentration range $10^{-7} < C < 10^{-3}$ to ensure that the mixture was stable; i.e., there was no depletion of the $CCl_4$ through wall adsorption or chemical reaction. This stability was checked at the lower concentrations by monitoring the $Cl^-$ signal over a period of 1 hour at $C = 1.0 \times 10^{-6}$. The signal was constant at the 5% level.

Figure 8:
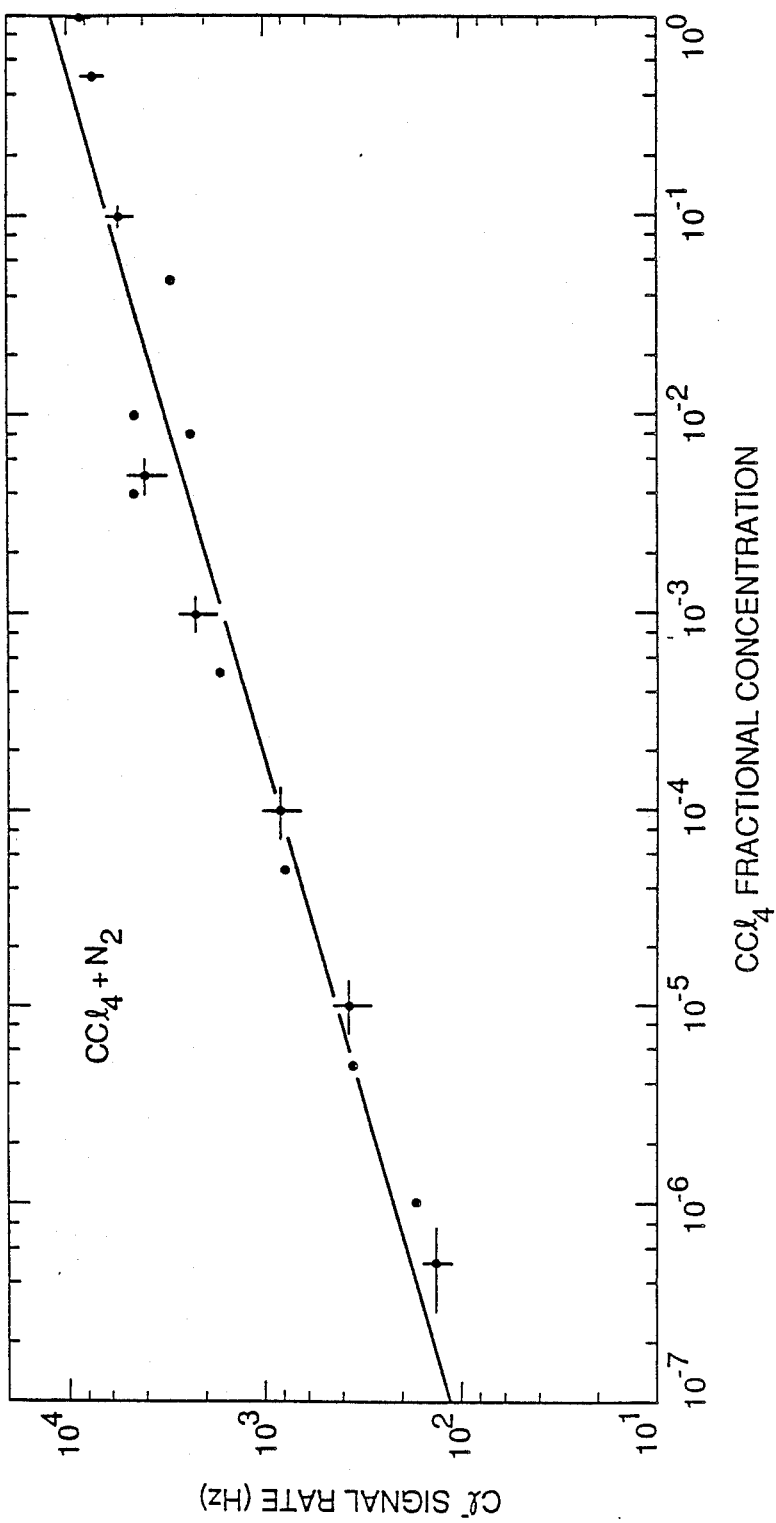
FIG. 8 is a graph of sensitivity evaluation data of the present invention using the method of standard additions analysis for various concentrations of $CCl_4$ in $N_2$.

Results of the standard additions calibration are shown in FIG. 8. The errors shown represent the quadrature sum of the statistical counting error and the error in reading the two pressure gauges. The electron current was $2.8 \times 10^{-6}$ amperes, and the pressure at the gas inlet only was estimated to be in the range $10^{-7}$ to $10^{-6}$ torr. One sees in FIG. 8 a uniform decrease of signal with concentration from 8.4 kHz at C=1.0 to 130 Hz at $C=5.0 \times 10^{-7}$. It is believed that this lower limit can be extended to the $10^{-8}$ range in a straightforward fashion, mainly by increasing the duty cycle of the ion extraction by a factor of 16.

Although preferred embodiments of the invention have been described and illustrated herein, it is recognized that modifications, improvements and equivalents may readily occur to those skilled in this art, particularly in improvements on electron current, beam size, collision volume and the like, which are currently being examined. Consequently, it is intended that the claims be interpreted to cover such modifications, improvements and equivalents.

We claim:

1. An in-line reversal electron high-current ionizer detector comprising
   means for producing a beam of free electrons,
   means for electrostatically focusing a beam of said free electrons along a predetermined beam axis into a collimated beam of electrons with zero longitudinal and radial velocity at a plane which establishes a reversal region of electrons,
   a channel for introducing into said reversal region a sample gas to be ionized,
   a mass analyzer in line with said beam axis,
   ion focusing means for extracting and focusing said ions into said mass analyzer axially in line with said electron beam,
   means for periodically switching said electron focusing means on and off, and
   means for periodically switching said ion focusing and extraction means off and on in phase with switching said electron focusing means on and off, whereby upon switching off said electron focusing means, said ion focusing and extraction means is switched on, and vice versa.

2. An in-line reversal electron high-current ionizer detector as defined in claim 1 wherein said means for electrostatically focusing said beam of electrons focuses said reversal plane to be positioned where said sample gas is introduced through said channel for efficient production of negative ions by zero-energy attachment of electrons to particles of said sample gas.

3. An in-line reversal electron high-current ionizer detector as defined in claim 2 wherein
   said means for electrostatically focusing said beam of electrons is comprised of three shaped electrodes, a first shaped electrode at a positive potential for focusing said electrons into a beam of predetermined diameter, a second shaped electrode at a negative potential for causing electrons in said beam of predetermined diameter to follow a path parallel to the beam axis, and a third electrode at a more negative potential than said second electrode for reversing said electrons, and
   said means for focusing and extracting negative ions is comprised of said first electrode switched to a negative potential while said second electrode is switched to zero potential to form a negative ion repeller lens, and said third electrode is switched to a positive potential to extract said negative ions.

4. An in-line reversal electron high-current ionizer detector as defined in claim 1 wherein said electrostatically focusing means establishes said reversal plane at a position downstream from where said sample gas is introduced through said channel, whereby free electrons of predetermined energy make two passes across said sample gas for efficient production of positive ions by bombardment of said sample gas particles with electrons.

5. An in-line reversal electron high-current ionizer detector as defined in claim 4 wherein said means for electrostatically focusing said beam of electrons is comprised of three shaped electrodes, a first shaped electrode at a positive potential for focusing said electrons into a beam of predetermined diameter, a second shaped electrode at a negative potential for causing electrons in said beam of predetermined diameter to follow a path parallel to the beam axis, and a third electrode to a more negative potential than said second electrode for reversing said electrons, said negative potentials of said second and third electrodes being selected for reversing said electrons in their parallel paths at a plane downstream from where said sample gas is introduced, and said means for focusing and extracting positive ions is comprised of said first electrode switched to a positive potential while said second electrode is switched to zero potential to form a positive ion repeller lens, and said third electrode switched to a more negative potential to extract said positive ions.

* * * * *